(12) United States Patent
Navia et al.

(10) Patent No.: US 10,039,644 B2
(45) Date of Patent: Aug. 7, 2018

(54) DEVICE, SYSTEM, AND METHOD FOR TREATING A REGURGITANT HEART VALVE

(71) Applicant: THE CLEVELAND CLINIC FOUNDATION, Cleveland, OH (US)

(72) Inventors: Jose L. Navia, Shaker Heights, OH (US); Samir Kapadia, Chagrin Falls, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 189 days.

(21) Appl. No.: 14/737,591

(22) Filed: Jun. 12, 2015

(65) Prior Publication Data

US 2015/0359632 A1 Dec. 17, 2015

Related U.S. Application Data

(60) Provisional application No. 62/011,294, filed on Jun. 12, 2014.

(51) Int. Cl.
*A61F 2/24* (2006.01)

(52) U.S. Cl.
CPC .......... *A61F 2/2454* (2013.01); *A61F 2/2442* (2013.01); *A61F 2/2457* (2013.01); *A61F 2230/0069* (2013.01)

(58) Field of Classification Search
CPC ................. A61F 2/2418; A61F 2/2445; A61F 2220/0016; A61F 2/2457; A61F 2/2442; A61F 2250/0004; A61F 2230/0034; A61F 2250/001; A61F 2/2451; A61F 2/2481; A61F 2002/249; A61F 2002/8483; A61F 2230/0004; A61F 2230/0063; A61F 2/848
See application file for complete search history.

(56) References Cited

U.S. PATENT DOCUMENTS

| | | | |
|---|---|---|---|
| 5,961,440 A | 10/1999 | Schweich, Jr. et al. | |
| 6,077,214 A | 6/2000 | Mortier et al. | |
| 6,231,561 B1* | 5/2001 | Frazier | A61B 17/00234 604/500 |
| 8,252,050 B2 | 8/2012 | Maisano et al. | |
| 2010/0121435 A1* | 5/2010 | Subramanian | A61F 2/2445 623/2.11 |
| 2010/0298929 A1 | 11/2010 | Thornton et al. | |
| 2013/0023985 A1* | 1/2013 | Khairkhahan | A61F 2/2466 623/2.38 |

FOREIGN PATENT DOCUMENTS

WO 2004112651 A2 12/2004

OTHER PUBLICATIONS

International Search Report and Written Opinion for PCT/US2015/035459, dated Sep. 4, 2015, pp. 1-12.

* cited by examiner

*Primary Examiner* — Ann Schillinger
(74) *Attorney, Agent, or Firm* — Tarolli, Sundheim, Covell & Tummino LLP

(57) ABSTRACT

In one aspect of the present disclosure, a device for treating a regurgitant heart valve in a subject can include a flexible, elongated body having a central chordae support portion disposed between first and second arms. The first and second arms can include first and second lumens, respectively, extending longitudinally therethrough. A method of treating a regurgitant heart valve in a subject is also provided.

9 Claims, 20 Drawing Sheets

DEVICE, SYSTEM, AND METHOD FOR TREATING A REGURGITANT HEART VALVE

RELATED APPLICATION

This application claims priority from U.S. Provisional Application No. 62/011,294, filed 12 Jun. 2014, the subject matter of which is incorporated herein by reference in its entirety.

TECHNICAL FIELD

The present disclosure relates generally to a devices, systems, and methods for treating dysfunctional heart valves, and more particularly to a device, system, and method for preventing or mitigating heart valve regurgitation.

BACKGROUND

The opening and closing of heart valves occur primarily as a result of pressure differences. For example, the opening and closing of the mitral valve occurs as a result of the pressure differences between the left atrium and the left ventricle. During ventricular diastole, the venous return of blood from the pulmonary veins into the left atrium causes the pressure in the atrium to exceed that in the left ventricle. As a result, the mitral valve opens and allows blood to enter the left ventricle. As the left ventricle contracts during ventricular systole, the intraventricular pressure rises above the pressure in the atrium and pushes the mitral valve shut.

When the high pressure produced by contraction of the left ventricle pushes the valve leaflets too much, the leaflets become everted and prolapse results. This is normally prevented by contraction of the papillary muscles within the left ventricle, which are connected to the mitral valve leaflets by the chordae tendineae (chords). Contraction of the papillary muscles is simultaneous with the contraction of the left ventricle and serves to keep healthy mitral valve leaflets tightly shut at peak contraction pressures.

Mitral valve malfunction can stem from a variety of etiologies. For example, the causes of mitral regurgitation can range from intrinsic disease of the leaflets (e.g., mainly due to degenerative disease in patients with mitral valve prolapse), to functional mitral regurgitation (FMR), in which the valve is anatomically normal but stretched due to tethering and annular dilatation. Although mitral regurgitation in intrinsic disease occurs initially as leaflet disease, secondary annular dilatation occurs in the large majority of patients by the time they present for treatment. The larger proportion of patients with mitral regurgitation includes those without intrinsic disease of the leaflets, i.e., FMR.

Surgical correction of FMR is based upon overcorrection of concomitant annular dilatation using an undersized, complete, and rigid annuloplasty ring that is intended to reduce the diameter of the mitral annulus and allow for leaflet coaptation. Although complete correction of mitral regurgitation has been surgically demonstrated, an important recurrence of mitral regurgitation after annuloplasty valve repair is common (25%) because the left ventricle continues to dilate or remodel, thereby causing further tethering of the mitral leaflets.

SUMMARY

In one aspect of the present disclosure, a device for treating a regurgitant heart valve in a subject can comprise a flexible, elongated body having a central chordae support portion disposed between first and second arms. The first and second arms can include first and second lumens, respectively, extending longitudinally therethrough.

In another aspect of the present disclosure, a system for treating a regurgitant heart valve in a subject can comprise a flexible elongated body, a first anchoring catheter, and a second anchoring catheter. The elongated body can comprise a central chordae support portion disposed between first and second arms. The first and second arms can include first and second lumens, respectively, extending longitudinally therethrough. The first anchoring catheter can be disposed in, and at least partially extend through, the first lumen. The second anchoring catheter can be disposed in, and at least partially extend through, the second lumen.

In another aspect of the present disclosure, a method is provided for treating a heart valve in a subject. A device comprising a flexible, elongated body having a central chordae support portion disposed between first and second arms is provided. The first and second arms include first and second lumens, respectively, extending longitudinally therethrough. The device is positioned in a heart chamber of the subject so that at least a portion of the central chordae support portion is in direct contact with a chordae tendineae associated with the heart valve. The device is anchored to an anchor heart tissue of the subject so that the central chordae support member displaces the chordae tendineae associated with the heart valve, along with an affected heart tissue, toward the anchor heart tissue and thereby improves cardiac functioning by creating a reverse remodeling of the heart chamber and improving valve leaflet coaptation.

In another aspect of the present disclosure, a method is provided for treating a heart valve in a subject. A device comprising a flexible, elongated body having a central chordae support portion disposed between first and second arms is provided. The first and second arms include first and second lumens, respectively, extending longitudinally therethrough. The device is implanted in a heart chamber of the subject so that at least a portion of the central chordae support portion is in direct contact with a chordae tendineae associated with the heart valve. The central chordae support member displaces the chordae tendineae associated with the heart valve toward an anchor heart tissue and improves cardiac functioning by creating a reverse remodeling of the heart chamber and improving valve leaflet coaptation.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1A:
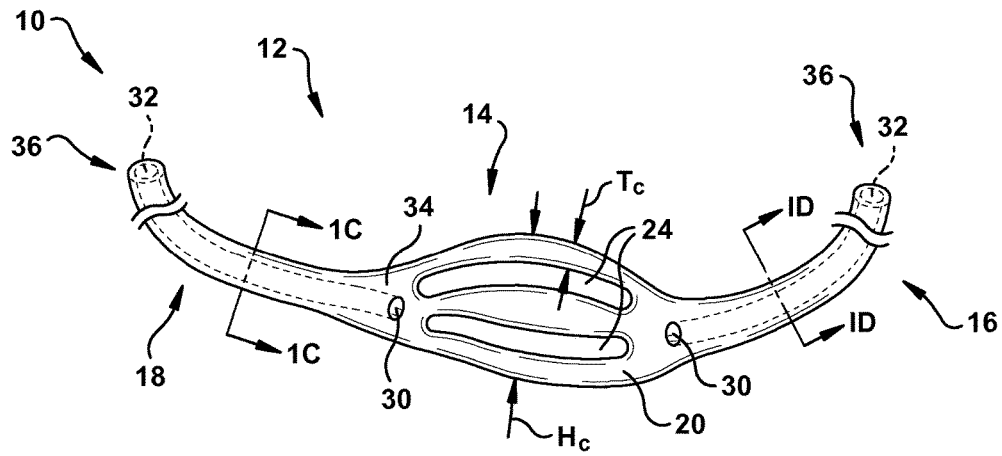
FIGS. 1A-B illustrate a device for treating a regurgitant heart valve in a subject constructed in accordance with an aspect of the present disclosure.

Unless defined otherwise, all technical and scientific terms used herein have the same meaning as is commonly understood by one of skill in the art to which the present disclosure pertains.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the terms "treat" or "treating" can refer to therapeutically regulating, preventing, improving, alleviating the symptoms of and/or reducing the effects of a regurgitant heart valve. As such, treatment also includes situations where a regurgitant heart valve, or at least a symptom associated therewith, is completely inhibited, e.g., prevented from happening or stopped (e.g., terminated) such that the subject no longer suffers from the regurgitant heart valve, or at least the symptom(s) associated therewith.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Overview

The invention comprises, consists of, or consists essentially of the following features, in any combination.

The present disclosure relates generally to a devices, systems, and methods for treating dysfunctional heart valves, and more particularly to a device, system, and method for preventing or mitigating heart valve regurgitation. The present disclosure provides a trans-catheter device, system, and related method for percutaneous treatment of subjects suffering from a regurgitant heart valve (e.g., ischemic mitral regurgitation and/or secondary tricuspid regurgitation) without removing leaflet tissue and/or placating/deforming the mitral valve annulus. As described in more detail below, the presently disclosed device, in some instances, pulls or displaces the posterior mitral leaflet subvalvular apparatus (e.g., the chordae tendineae and papillary muscles associated with the posterior mitral leaflet) toward the interventricular septum. In such instances, the presently disclosed device advantageously provides a reverse-remodeling effect whereby the angle of mitral leaflet coaptation is normalized, the surface of mitral leaflet coaptation is increased, and the left ventricle is restored to a more normal size and shape to prevent or eliminate regurgitation.

In other words, the disclosed device may assist with remodeling a mitral and/or tricuspid cardiac valve, supporting the leaflets as well as the free-edge, and sub-valvular apparatus, to correct and improve leaflet coaptation and to resolve valve regurgitation. For example, embodiments of the disclosed device include a free-edge leaflet and sub-valvular supporting mechanism that prevents valve leaflets tethering and the mitral and tricuspid valve regurgitation during systole, by correcting and normalizing the level and angle of leaflet coaptation.

The disclosed device can be introduced and delivered under echocardiographic and/or fluoroscopic guidance through a transcatheter or percutaneous approach with a flexible electromagnetic or mechanical adjustment catheter antegrade transeptally or retrograde trans femoral, or by minimally invasive surgical procedure trans atrial, trans apical, trans aortic, trans carotid, and/or trans subclavian artery approaches.

The disclosed device can have at least two different stable positions (e.g., related to the embodiments discussed in detail below), which can be adjusted depending on the anatomic leaflet and sub-valvular apparatus configuration, and the free-edge leaflet coaptation angle, to obtain normal correction such as by mechanical or electromagnetic adjustment, optionally through a flexible catheter by echo guidance.

The disclosed device also can have at least two different stable positions (e.g., related to the embodiments discussed in detail below), which can be adjusted depending on the anatomic leaflet and sub-valvular apparatus configuration, and the free-edge leaflet coaptation angle, to obtain normal correction such as by transcatheter or percutaneous approach with a flexible electromagnetic or mechanical adjustment catheter, optionally by transseptal, transaortic, transapical, and/or transatrial approach, under echocardiographic guidance.

The disclosed device can correct the unbalance angle of leaflets coaptation of the regurgitant valve. In other words, this device can operate as a "coaptation alignment support", and also, optionally, move the left ventricular wall more medially in order to obtain better mitral and/or tricuspid valve competency and, in some instances, may help to develop left and/or right ventricle reverse remodeling.

Device

Figure 1B:
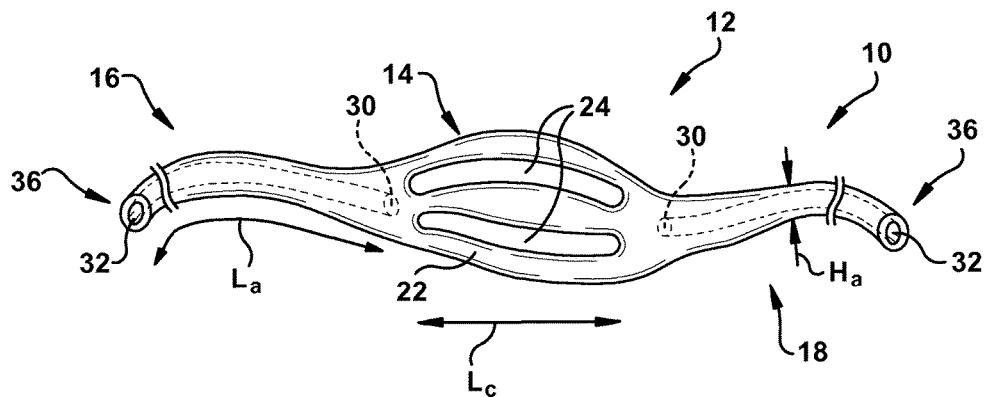
Figure 1C:
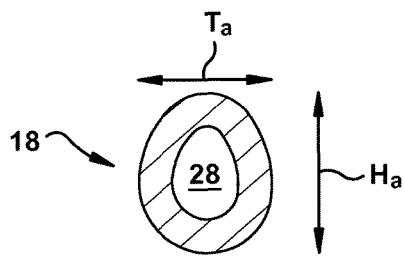
FIG. 1C is a cross-sectional view taken along Line 1C-1C in FIG. 1A.
Figure 1D:
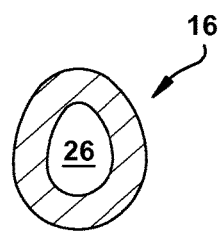
FIG. 1D is a cross-sectional view taken along Line 1D-1D in FIG. 1A.

As representative of one aspect of the present disclosure, FIGS. 1A-B illustrate a device 10 for treating regurgitation of blood flow through a diseased heart valve, such as a regurgitant mitral valve. The device 10 can have a sling-shaped configuration (i.e., a short central strap portion attached to longitudinally opposed elongate support strands) and be sized and dimensioned for implantation into the left ventricle of a subject (e.g., via a percutaneous trans-catheter approach). The device 10 can be made of one or a combination of biocompatible materials (e.g., PTFE, ePTFE, PEEK) that impart all or only part of the device with flexible or supple properties. It will be appreciated, however, that certain portions of the device 10 may be constructed with a material (or materials) that impart certain portion(s) of the device with rigid or semi-rigid properties.

As shown in FIGS. 1A-B, the device 10 can comprise an elongated body 12 having a central chordae support portion 14 disposed between first and second arms 16 and 18. The central chordae support portion 14 can be defined by oppositely disposed first and second surfaces 20 and 22 that define a thickness $T_c$. In effect, the second surface 22 comprises a contact surface, at least a portion of which can be sized and dimensioned to directly contact the chordae tendineae. The second surface 22 can thus be made of one or more materials so that the second surface is soft or atraumatic and does not damage the chordae tendineae when the device 10 is implanted.

In other words, the central chordae support portion 14 may include at least one contact surface (e.g., first and/or second surfaces 20 and 22) configured to directly contact one or more chordae tendineae, the at least one contact surface having an area that is at least one of less than, about equal to, and greater than the footprint of the first and/or second arms 16 and 18. (The "footprint" is the projection or shadow of the three-dimensional subject structure onto a two-dimensional underlying surface.) For many use environments of the disclosed device 10, the contact surface will have an area that is greater than the footprint of a corresponding (to the length of the contact surface) length of both of the first and second arms 16 and 18, as shown in the Figures.

The central chordae support portion 14 can also be defined by a length $L_c$ (FIG. 1B) and a height $H_c$ (FIG. 1A). The height $H_c$ can be uniform or different (asymmetrical) across the length $L_c$ of the central chordae support portion 14. As shown in FIGS. 1A-B, for example, the height $H_c$ can be asymmetrical such that the central chordae support portion 14 has a chin strap-like (i.e., tapered-height on both sides, with a maximum height $H_c$ at approximately a mid-section of the length $L_c$) configuration.

In some instances, the central chordae support portion 14 can include one or more apertures 24 extending between the first and second surfaces 20 and 22. As shown in FIGS. 1A-B, the apertures 24 can have a substantially rectangular shape and extend essentially parallel to one another. It will be appreciated that the apertures 24 can have any other shape (e.g., oval, circular, rectangular, etc.) and be arranged in a variety of locations relative to one another. In some instances, the central chordae support portion 14 can include a plurality of apertures 24 to impart the central chordae support portion with a mesh-like configuration. Advantageously, the apertures 24 minimize the amount of material in contact with blood while also maximizing blood flow through and around the device 10 when implanted. It will also be appreciated that, in other instances, the central chordae support portion 14 may be free of any apertures 24.

The first and second arms 16 and 18 of the device 10 are connected to the central chordae support portion 14. In some instances, the first and second arms 16 and 18 are formed from the same material as the central chordae support portion 14 and, thus, the elongated body 12 is a single, unitary structure. In other instances, the first and second arms 16 and 18 can be separate structures that are securely joined to the central chordae support portion 14 (e.g., by sutures, clips, adhesive, or the like). As shown in FIG. 1B, each of the first and second arms 16 and 18 includes a thickness $T_a$, a height $H_a$, and a length $L_a$. The thickness $T_a$, the length $L_a$, and the height $H_a$ of the first and second arms 16 and 18 can be the same or different. In some instances, the height $H_a$ of the first and second arms 16 and 18 can be the same or different than the height $H_c$ of the central chordae support portion 14. In other instances, the second surface 22 of the central chordae support portion 14 can have an area that is less than, about equal to, or greater than the surface area of the first arm 16 and/or the second arm 18.

The first and second arms 16 and 18 can include first and second lumens 26 and 28, respectively, which extend longitudinally therethrough. As discussed in more detail below, the first and second lumens 26 and 28 can be configured to receive a variety of delivery devices, such as a guidewire or a catheter. Each of the first and second lumens 26 and 28 can extend between first and second openings 30 and 32. As shown in FIGS. 1A-B, the first opening 30 of each of the first and second lumens 26 and 28 can be located immediately adjacent the central chordae support portion 14. Additionally, the first opening 30 of each of the first and second lumens 26 and 28 can be located on a first major surface 34 that partially defines the first and second arms 16 and 18. Each of the second openings 30 and 32 can be located at a distal end 36 of each of the first and second arms 16 and 18. Though the device is shown as including two lumens, it will be appreciated that the device 10 can include only one lumen or, alternatively, three or more lumens.

System

Figure 2:
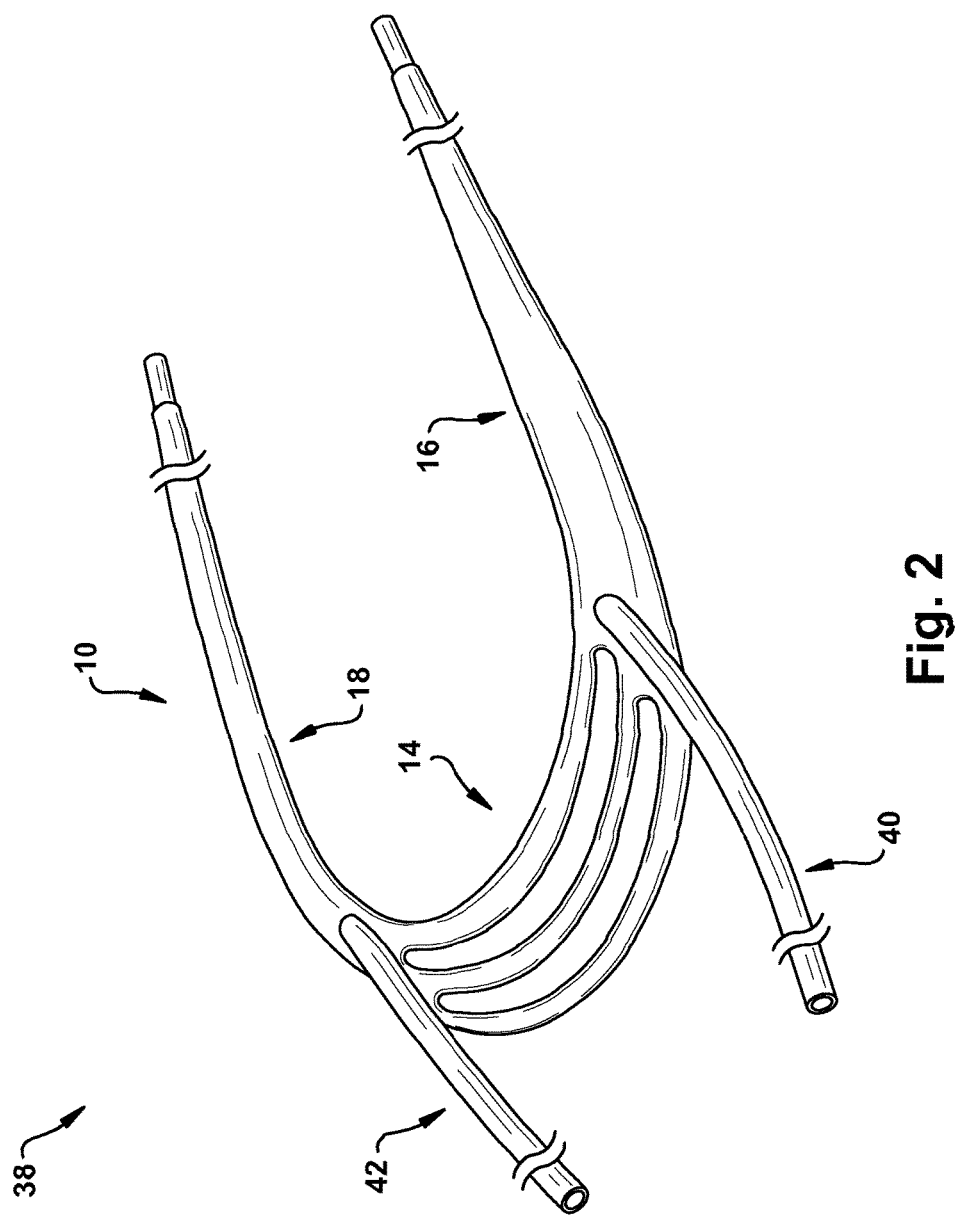
FIG. 2 is a perspective front view showing a system for treating a regurgitant heart valve in a subject constructed in accordance with an aspect of the present disclosure.

Another aspect of the present disclosure can include a system 38 (FIG. 2) for treating a regurgitant heart valve in a subject. The system 38 can comprise a device 10, a first anchoring catheter 40, and a second anchoring catheter 42. The device 10 can be identically or similarly constructed as the device shown in FIGS. 1A-B and described above. Each of the first and second anchoring catheters 40 and 42 can have an elongated, tubular shape and be made of one or a combination of biocompatible materials, such as PTFE, ePTFE, PEEK, etc. The first and second anchoring catheters 40 and 42 can be sized and dimensioned for insertion into the first and second lumens 26 and 28 of the device 10, respectively. In the assembled configuration of the system 38 shown in FIG. 2, the first and second anchoring catheters 40 and 42 can be disposed in, and at least partially extend through, the first and second lumens 26 and 28 (respectively) of the device 10. The first and second anchoring catheters 40 and 42 can be sized and dimensioned to suspend and position the device 10 in the left ventricle when the device is implanted in a subject. As discussed in more detail below, the first and second anchoring catheters 40 and 42 can be configured to receive a guidewire, which may then be used to convey one or more anchoring elements therethrough.

Method

Figure 4:
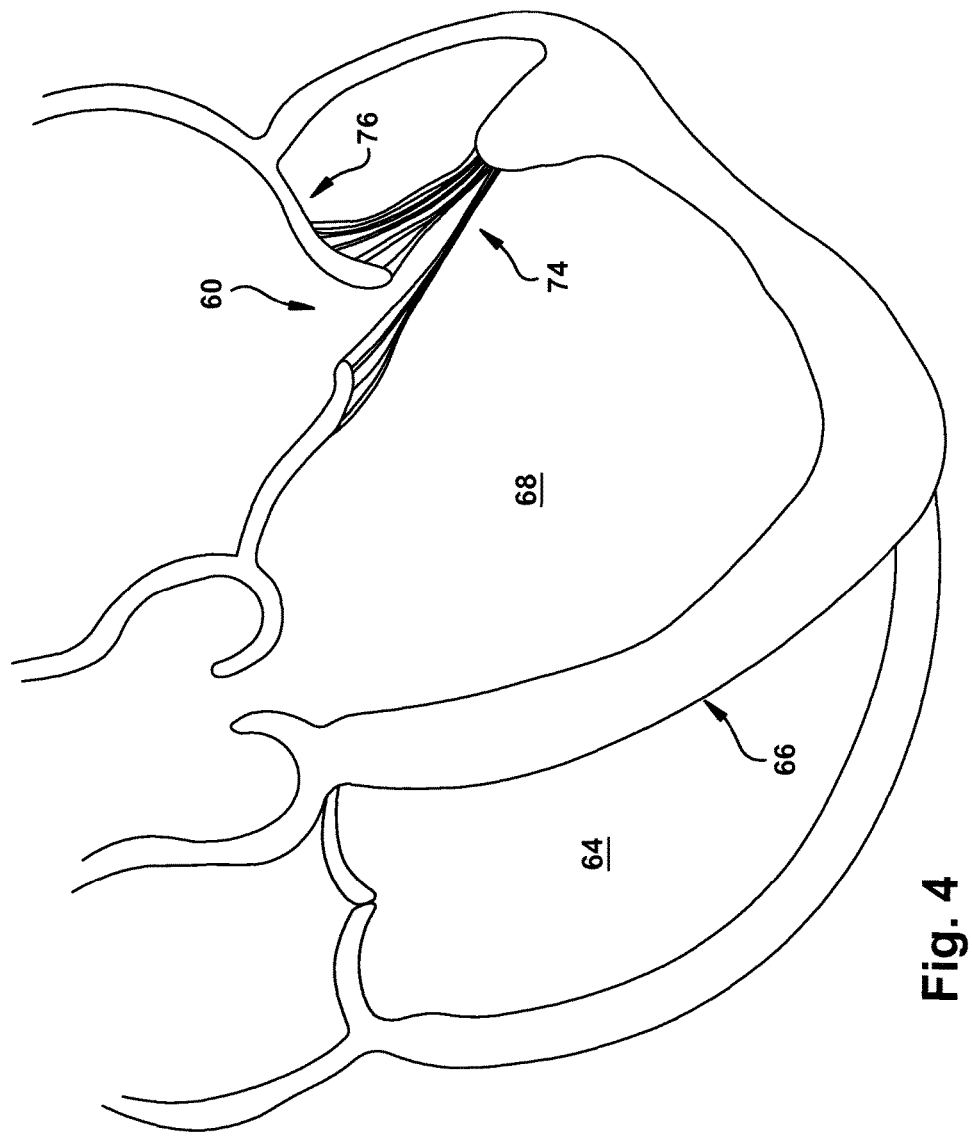
FIG. 4 is a schematic partial cross-sectional view of a human heart showing a regurgitant mitral valve caused by asymmetrical leaflet tethering.
Figure 5:
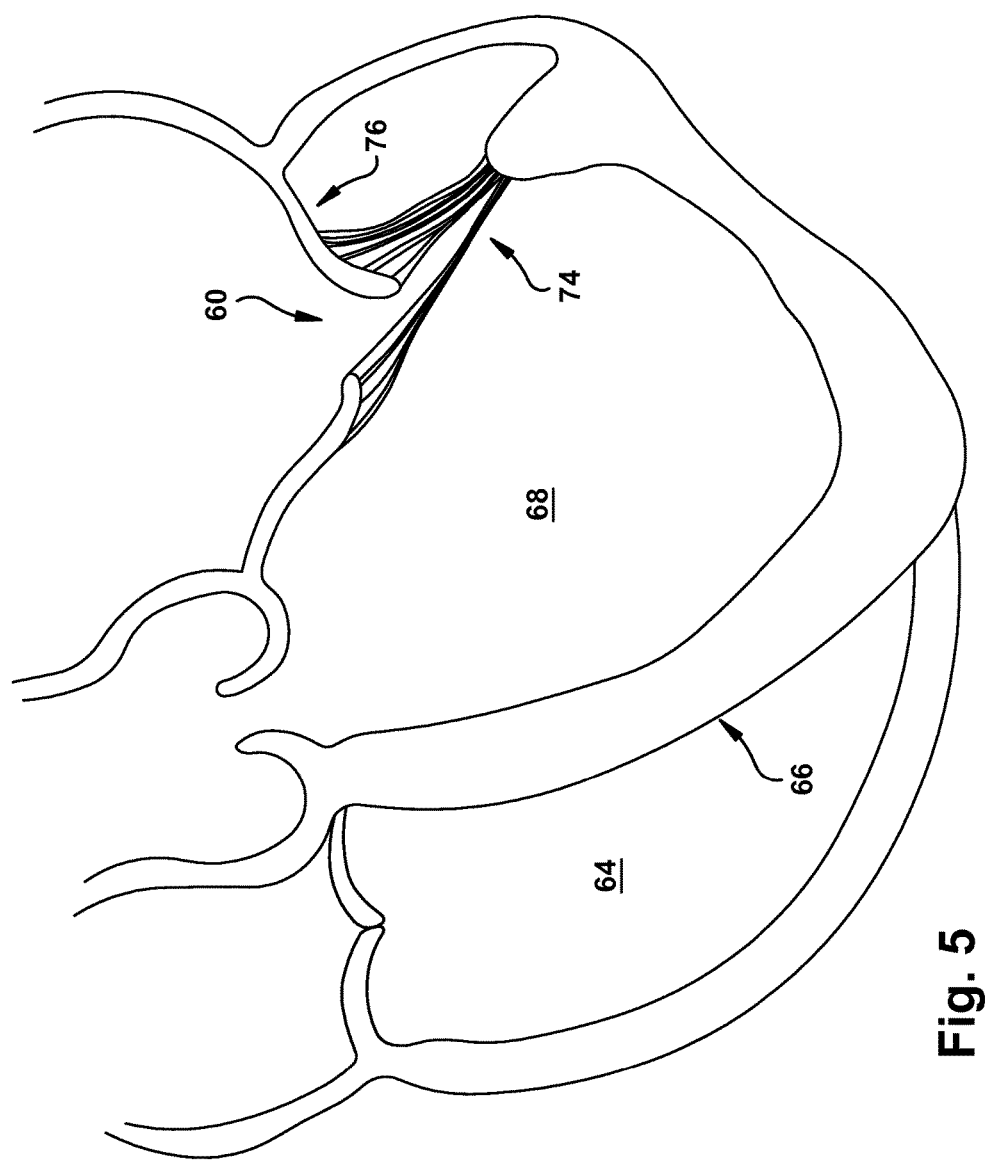
FIG. 5 is a schematic partial cross-sectional view of a human heart showing a regurgitant mitral valve caused by symmetrical leaflet tethering.

Another aspect of the present disclosure can include a method 44 (FIG. 3) for treating a regurgitant heart valve or a condition associated therewith, such as, in the depicted example, ischemic mitral regurgitation (IMR) or functional mitral regurgitation (FMR) associated with a regurgitant mitral valve. IMR and FMR can result from mitral leaflet tethering due to left ventricular remodeling. Heterogeneity in local or global left ventricular remodeling can result in differential tethering patterns and affect mitral valve function and the degree of mitral regurgitation. Illustrating examples of FMR are FIGS. 4-5, which show regurgitant mitral valves 60 as a result of asymmetrical leaflet tethering and symmetrical tethering, respectively. The method 44 of the present disclosure will be illustrated in terms of treating a regurgitant mitral valve 60. It will be appreciated that even though the method 44 is described below in terms of treating a regurgitant mitral valve 60, the method can alternatively be used to treat another heart valve, such as a regurgitant tricuspid valve (not shown). Likewise, it will be appreciated that even though the method 44 is described below using a percutaneous approach from the right ventricle across the interventricular septum into the left ventricle, the method can alternatively be used with, for example, a transcatheter or percutaneous approach with a flexible electromagnetic or mechanical adjustment catheter, optionally into any portion of the heart (e.g., a transseptal, transaortic, transapical, and/or transatrial approach), such as under echocardiographic guidance.

Figure 3:
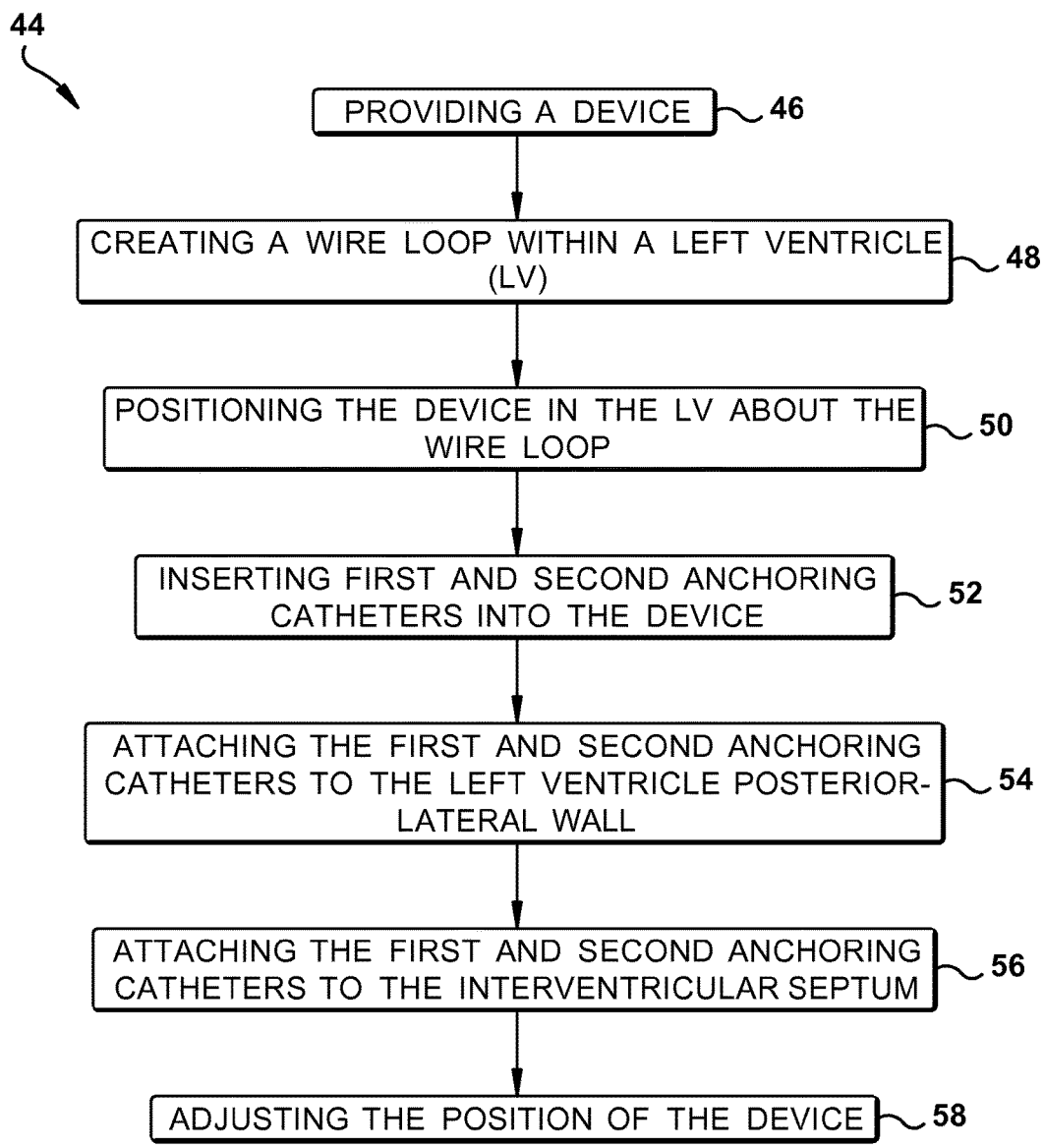
FIG. 3 is a process flow diagram illustrating a method for treating a regurgitant mitral valve in a subject in accordance with an aspect of the present disclosure.

Referring to FIG. 3, Step 46 of the method 44 can include providing a device 10. The device 10 can be configured in an identical or similar manner as the device described above. For example, the device 10 can comprise a flexible, elongated body 12 having a central chordae support portion 14 disposed between first and second arms 16 and 18, each of which includes first and second lumens 26 and 28 (respectively) that extend longitudinally therethrough.

After selecting an appropriate device 10, a first guidewire 62 (FIG. 6) can be inserted into the vasculature of the subject and then advanced into any suitable heart chamber—here, for the sake of discussion, into the right ventricle 64. Using the Seldinger technique, for example, the first guidewire 62 can be advanced through the jugular vein (not shown) or a femoral vein (not shown) into the right ventricle 64. Next, the first guidewire 62 can be advanced across the interventricular septum 66 into the left ventricle 68. Once a distal end 70 of the first guidewire 62 is positioned in the left ventricle 68, a device delivery catheter 72 can be advanced over the first guidewire 62 into the left ventricle 68. The first guidewire 62/device delivery catheter 72 can then be advanced behind and around the chordae tendineae 74 associated with the posterior mitral valve leaflet 76. (It should be understood that no septal puncture is required for some other insertion paths, and that, regardless of the insertion path taken, the distal end 70 of the first guidewire 62, or any other desired structure of the system 38, can be placed into any desired heart chamber by one of ordinary skill in the art using the structures and principles described herein.)

Figure 6:
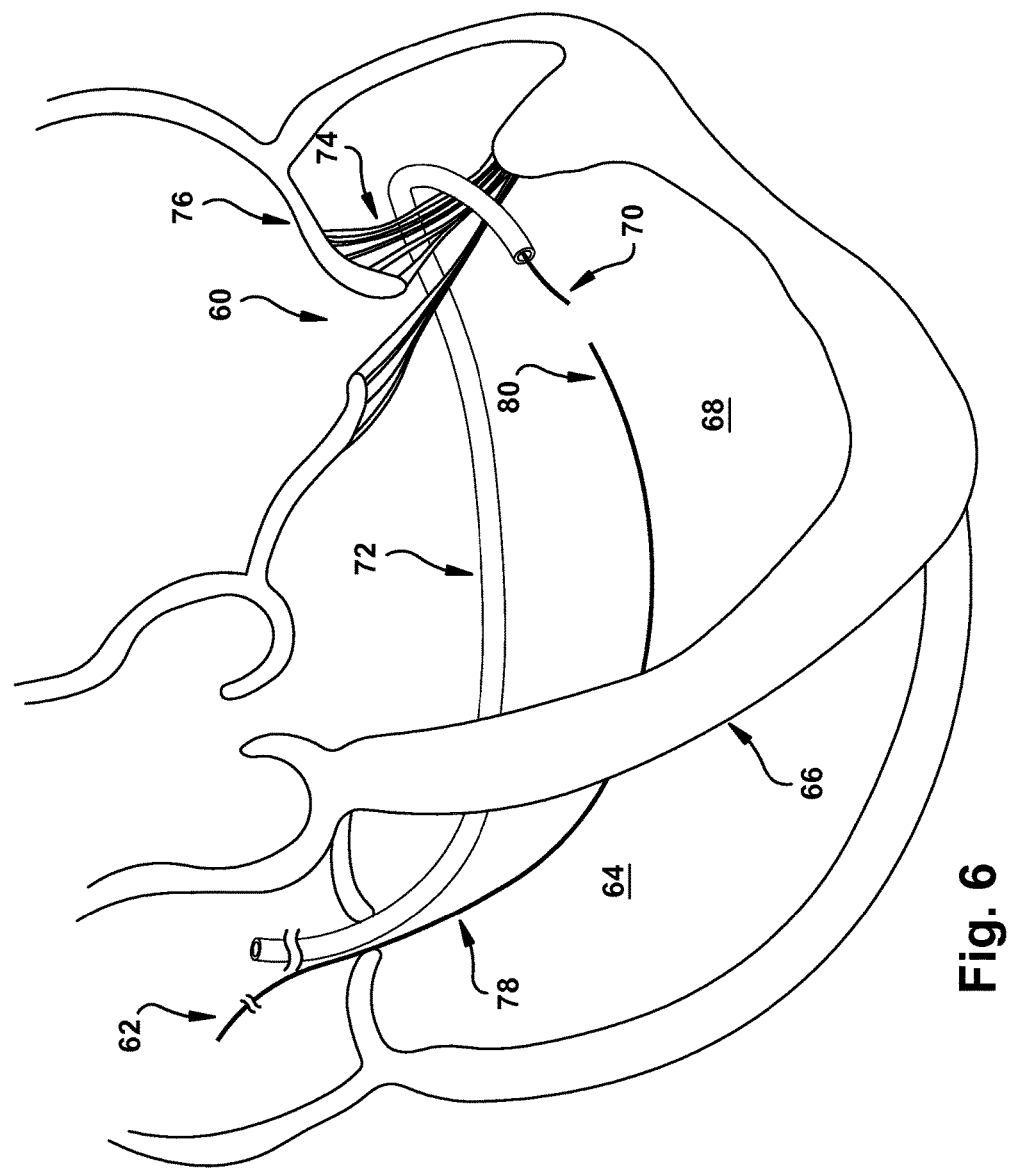
FIG. 6 is a schematic illustration showing creation of a wire loop within the left ventricle of FIG. 4.

At Step 48, a wire loop can be created in the left ventricle 68. As shown in FIG. 6, a second guidewire 78 can be inserted into the right ventricle 64 (e.g., using the Seldinger technique) and then advanced across the interventricular septum 66. A second catheter (not shown) can then be advanced over the second guidewire 78 into the left ventricle 68. A distal end 80 of the second guidewire 78 and the second catheter can be positioned immediately adjacent the distal end 70 of the first guidewire 62. Next, a snare (not shown) can be threaded through the second catheter and progressively fed therethrough until the snare catches the distal end 70 of the first guidewire 62, thereby forming a wire loop around the chordae tendineae 74 associated with the posterior mitral valve leaflet 76.

Figure 7:
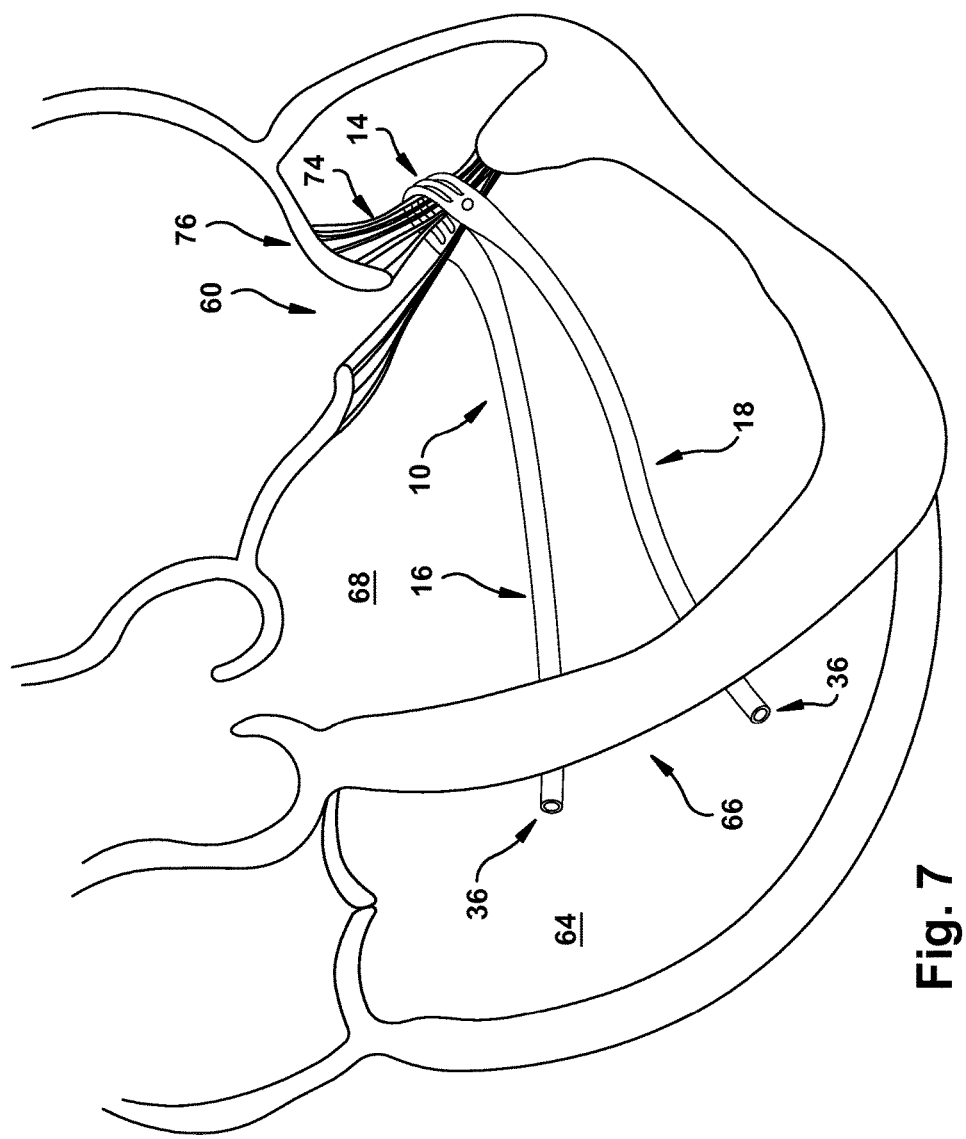
FIG. 7 is a schematic illustration showing the device of FIGS. 1A-B positioned in the left ventricle.

Once the wire loop has been formed, the device 10 can be loaded into the device delivery catheter 72. The device 10 can then be advanced through the device delivery catheter 72, along the wire loop, until the device is positioned within the left ventricle 68 (Step 50). In particular, the device 10 can be advanced along the wire loop until the distal end 36 of the second arm 18 is located in the right ventricle 64 (as shown in FIG. 7). Positioning the device 10 at Step 50 results in the central chordae support portion 14 of the device 10 partially encircling the chordae tendineae 74 associated with the posterior mitral valve leaflet 76, as well as the distal end 36 of each of the first and second arms 16 and 18 being located in the right ventricle 64. Sutures, hooks, barbs, screws, flexible discs, loop members, bands, rings, or any other aid mechanism may be provided to any structure of the device 10, and be used in cooperation with any patient tissue structure, to affix the device 10 to the patient tissue, whether or not the chordae are permitted to slide on these aid mechanisms and/or the central chordae support portion 14 of the device 10. Similarly, it is contemplated that a material and/or coating/impregnate could be provided to at least the central chordae support portion 14 of the device 10 to either encourage or discourage tissue ingrowth, as desired for a particular patient treatment plan.

Optionally, anchors of any suitable type (omitted from FIG. 7) could be provided at the distal end 36 of each of the first and second arms 16 and 18 within the right ventricle, before or after a length of the first and second arms 16 and 18 are optionally adjusted, to tension the first and second arms and thus place a tensile force on the chordae tendineae 74 via the central chordae support portion 14, thus completing the surgical procedure. However, it is also contemplated that additional structures could be installed, such as in the sequence described in Steps 52-56 of FIG. 3 and depicted in FIGS. 7-11.

Figure 8:
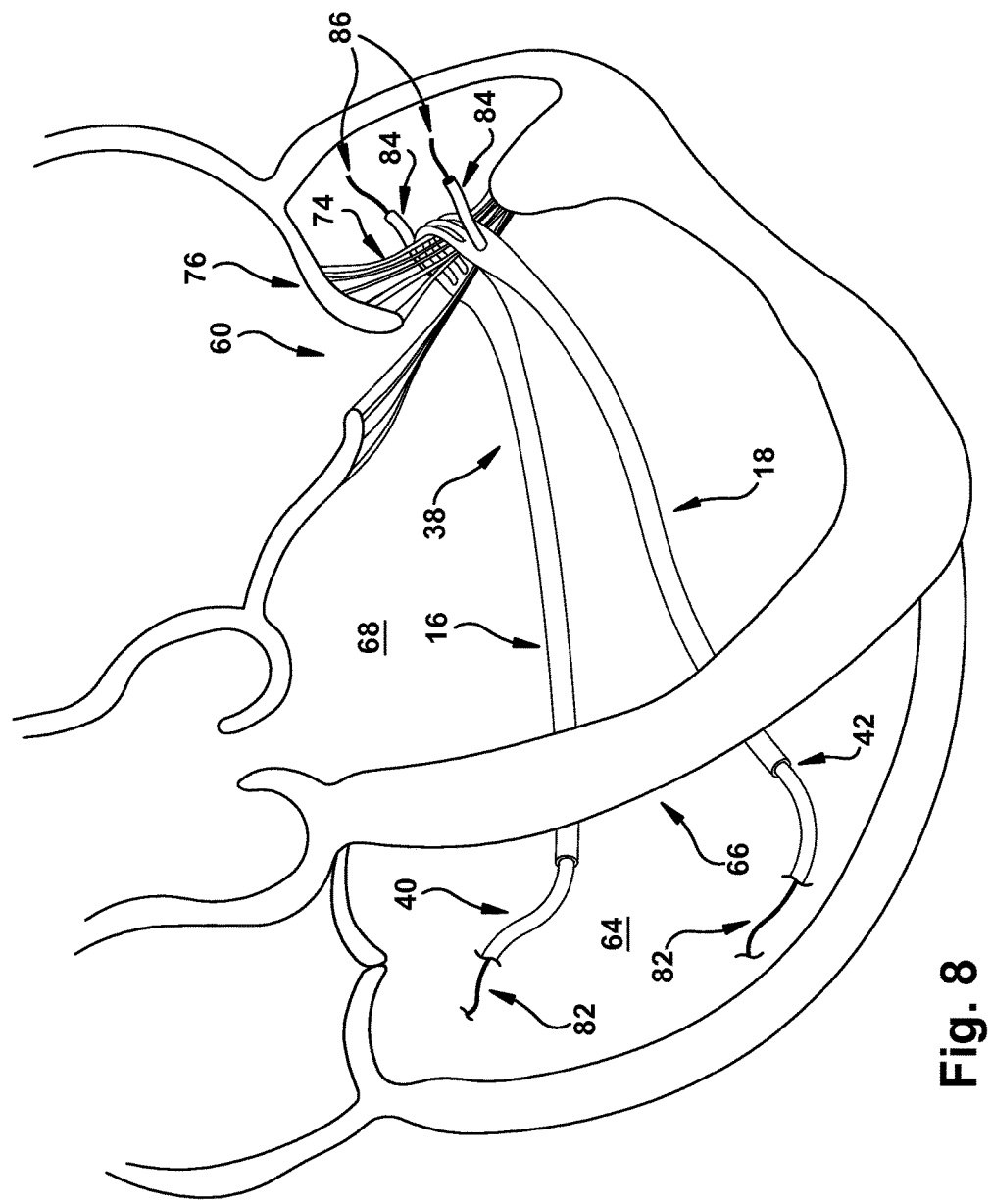
FIG. 8 is a schematic illustration showing first and second anchoring catheters being mated with the device of FIGS. 1A-B.

At Step 52, first and second anchoring catheters 40 and 42 (FIG. 8) can be advanced into the right ventricle 64 and inserted into the first and second lumens 26 and 28 of the first and second arms 16 and 18, respectively. As shown in FIG. 8, the first and second anchoring catheters 40 and 42 can be guided to (and through) the first and second lumens 26 and 28, respectively, using separate guidewires 82. The first and second anchoring catheters 40 and 42 can then be advanced through the first and second lumens 26 and 28 (respectively) until a distal end 84 of each of the first and second anchoring catheters 40 and 42 extends beyond the respective first opening 30 of the device 10. The distal end 84 of each of the first and second anchoring catheters 40 and 42 can then be advanced until it is substantially flush with the endocardial surface of the left ventricle posterior-lateral wall. Next, a distal end 86 of each of the separate guidewires 82 can be advanced through the left ventricle wall to reach the pericardial space, whereafter the first and second anchoring catheters 40 and 42 are progressively fed over the guidewires 82.

Figure 9:
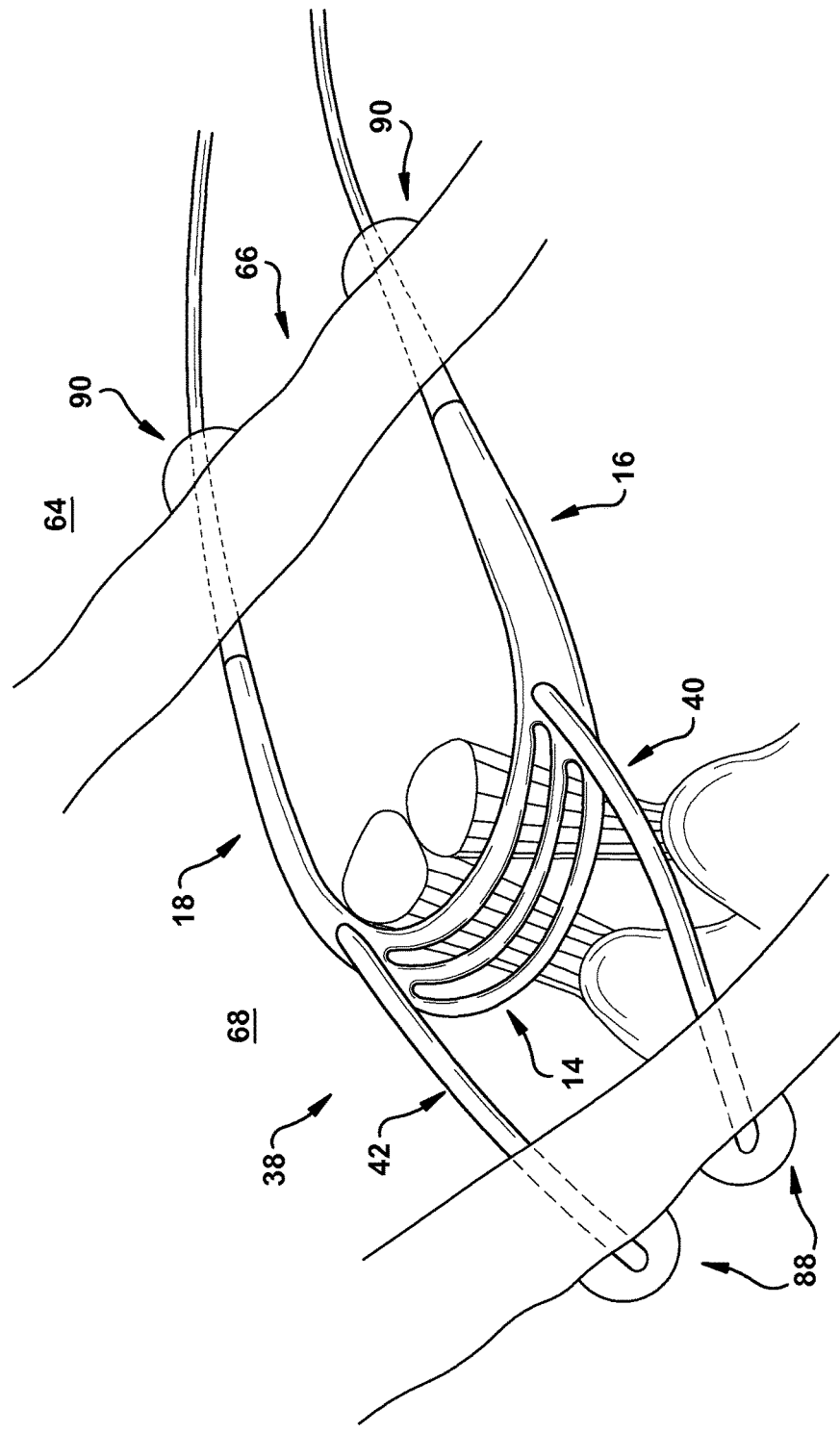
FIG. 9 is a schematic illustration showing the device of FIGS. 1A-B secured within the left ventricle.
Figure 10:
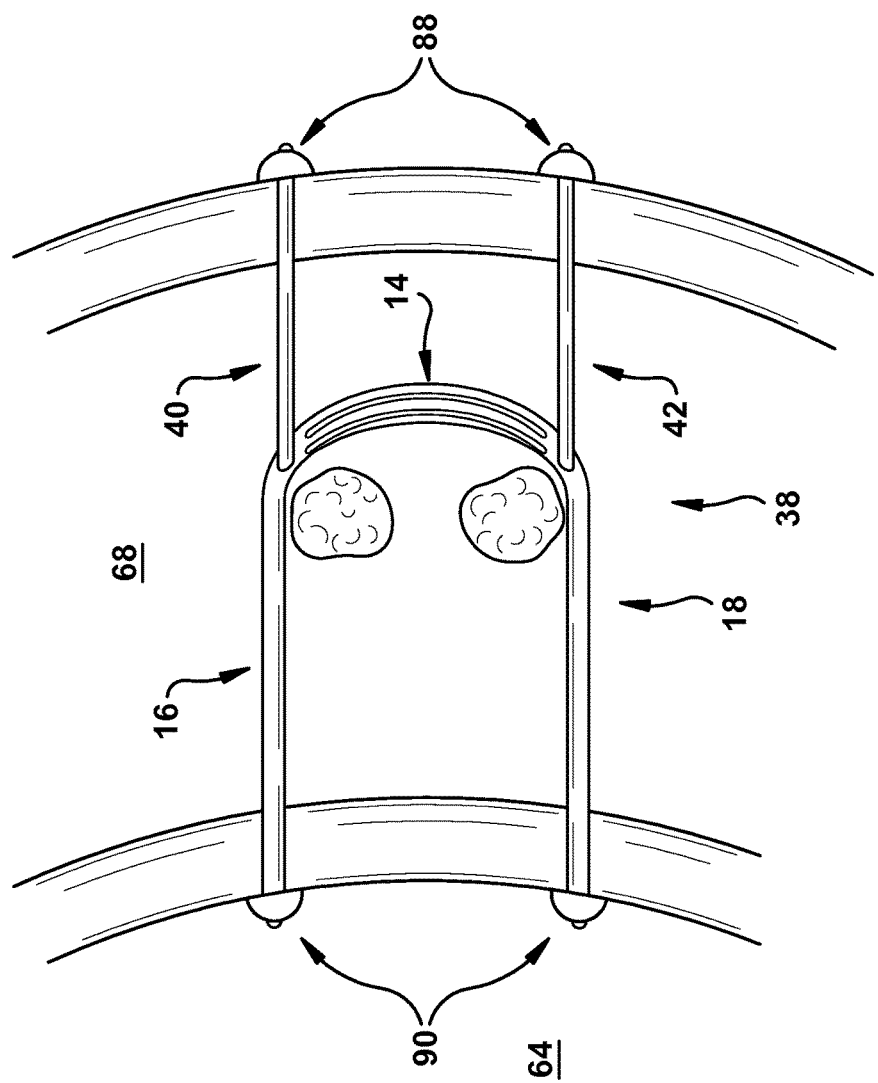
FIG. 10 is a schematic plan view of the device of FIGS. 1A-B.

The device can be anchored in the left ventricle 68 at Steps 54-56 of the method 44. First, for example, separate external left ventricle anchors 88 (e.g., single or double titanium anchors) (FIG. 9) can be advanced through the first and second anchoring catheters 40 and 42. The external left ventricle anchors 88 can then be deployed outside an affected heart tissue of the patient—here, the left ventricle posterior-lateral wall. Next, separate internal right ventricle anchors 90 (e.g., single or double titanium anchors) can be advanced over the separate guidewires 82 and then deployed to seat the internal right ventricle anchors on an anchor heart tissue of the patient—here, the right ventricle side of the interventricular septum 66. One example of an anchoring system that may be suitable for Steps 54-56 of the method 44 is commercially available from BIOVENTRIX Inc. (San Ramon, Calif.). The device 10, when properly anchored in the left ventricle 68, is illustrated in FIGS. 9-10.

At Step 58, the position of the device 10 and, in particular, the central chordae support portion 14, can be adjusted as needed to ensure proper mitral leaflet coaptation. For example, the external left ventricle anchors 88 and the internal right ventricle anchors 90 can be cinched (e.g., using echocardiographic guidance from the right ventricle 64) so that the central chordae support portion 14 and the first and second anchoring catheters 40 and 42 pull the posterior leaflet subvalvular apparatus (e.g., the chordae tendineae 74) along with the left ventricle wall toward the interventricular septum 66. The device 10 may also or instead be adjusted by tightening the distal ends 36 of the first and second arms 16 and 18, at the level of the sub-valvular apparatus. The valve competency can be tested by fluoroscopy, injecting contrast solution through the valve, and/or by echocardiographic guidance while the device 10 is percutaneously or surgically tightened or loosened.

Figure 11:
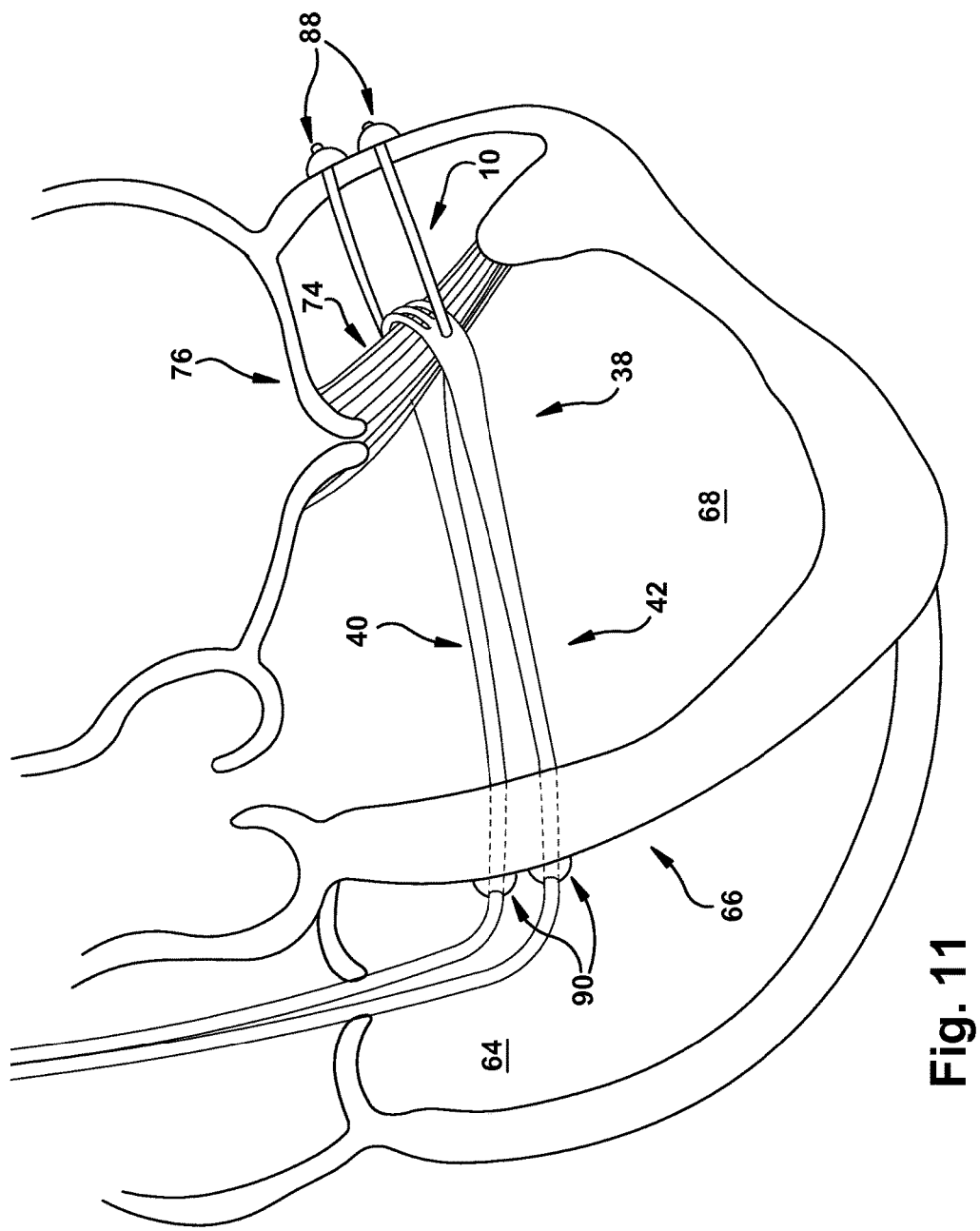
FIG. 11 is a schematic illustration showing the device of FIGS. 1A-B displacing the chordae tendineae associated with the posterior mitral valve leaflet, along with the postero-lateral left ventricle wall, toward the interventricular septum and thereby improving cardiac functioning by creating a reverse remodeling of a posterior left ventricular wall and improving valve leaflet coaptation

Consequently, as shown in FIG. 11, mitral regurgitation may be reduced, prevented, or eliminated by normalizing the angle of mitral leaflet coaptation, increasing the surface area of mitral leaflet coaptation, and restoring the left ventricle 68 to a more desired size and shape. Stated differently, the device 10 helps to correct the unbalance angle of leaflets coaptation of the regurgitant valve, such as by working as a "coaptation alignment support", and optionally also by moving the left ventricular wall more medially in order to obtain better mitral or tricuspid valve competency and/or by developing left and/or right ventricle reverse remodeling.

Figure 12:
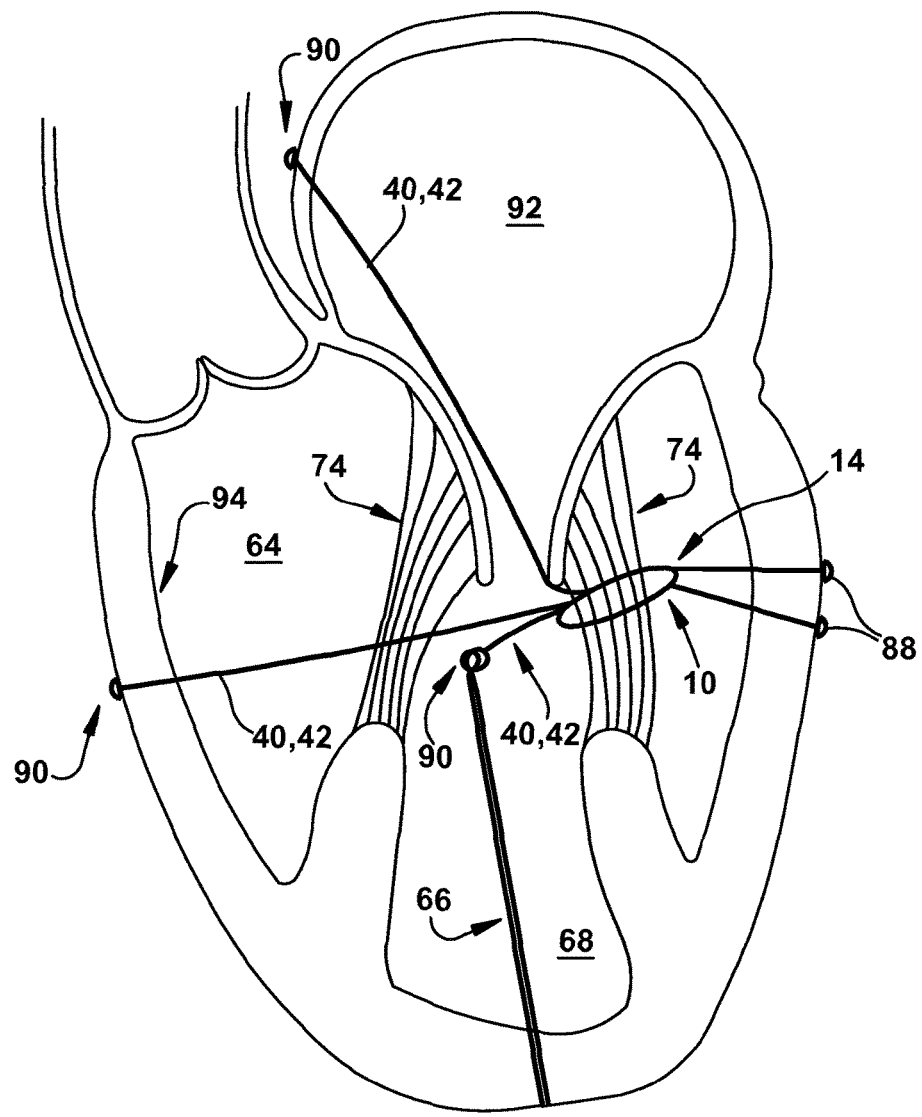
FIG. 12 is a schematic side view of an alternative configuration of the device of FIGS. 1A-1B.

It is contemplated that portions of the device (e.g., the distal ends 36) could include, or be attached to, a stent, hooks, barbs, screws, flexible discs, loop members, or any other desired aid mechanisms, to anchor the device 10 to anatomic heart structures such as, but not limited to, the ventricular wall, interventricular septal wall, interatrium septal wall, atrial wall, coronary sinus, pericardium, IVC, SVC, pulmonary veins, or any other desired patient tissue structures. For example, and as shown in FIG. 12, versions of the first and second anchoring catheters 40 and 42 are seen as being anchored to the left atrium 92 wall, the interatrial septum 94, and the interventricular septum 66—these various anchoring locations could be used together (as shown), in any combination with or without other anchoring locations, or singly. The system 38, or portions thereof, can also or instead be supported by additional anchoring mechanisms that are suspended from any suitable patient tissue structures.

Figure 13:
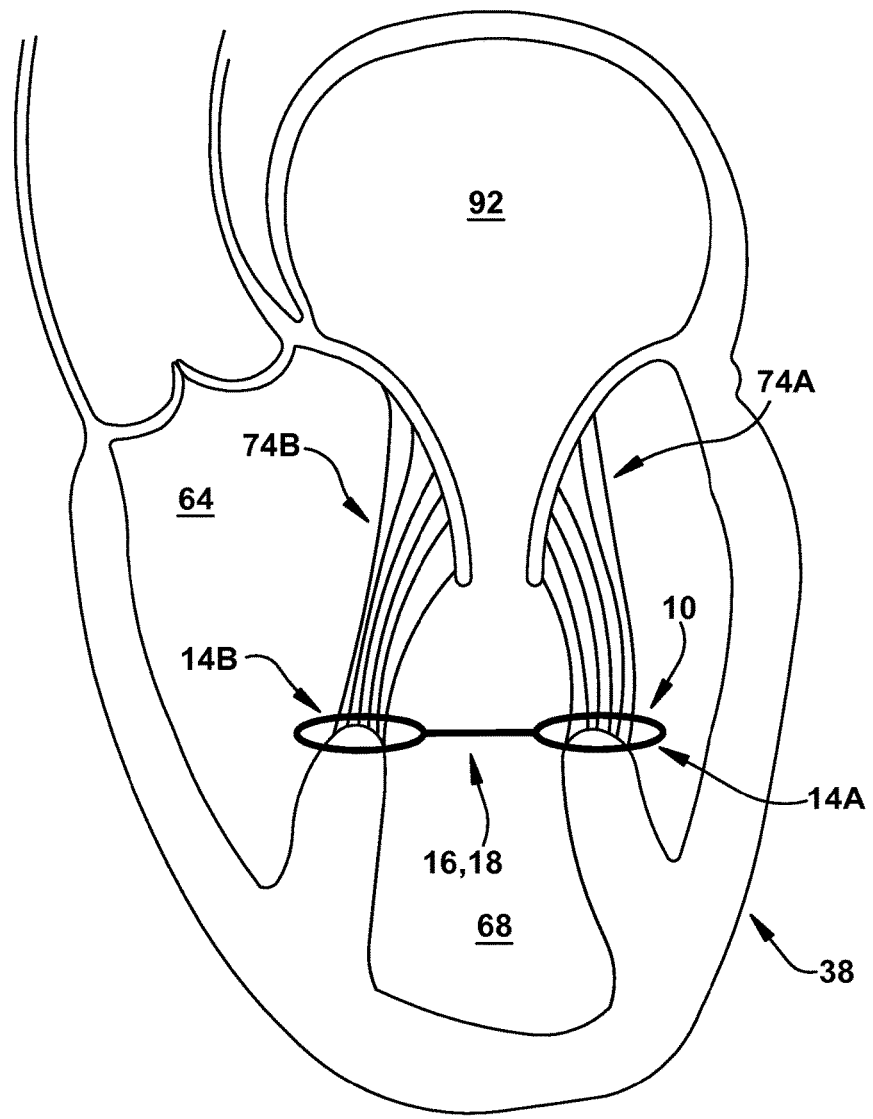
FIG. 13 is a schematic side view of an alternative configuration of the device of FIGS. 1A-1B.

FIG. 13 shows an alternate configuration of the device 10, wherein two central chordae support portions 14A and 14B are used to mutually tension two corresponding sets of chordae tendineae 74A and 74B, respectively. The first and second anchoring catheters 40 and 42 extending between the two central chordae support portions 14A and 14B to draw the associates chordae tendineae 74A and 74B closer together, thus coapting the associated valve leaflets and reducing or preventing unwanted regurgitation.

Figure 14:
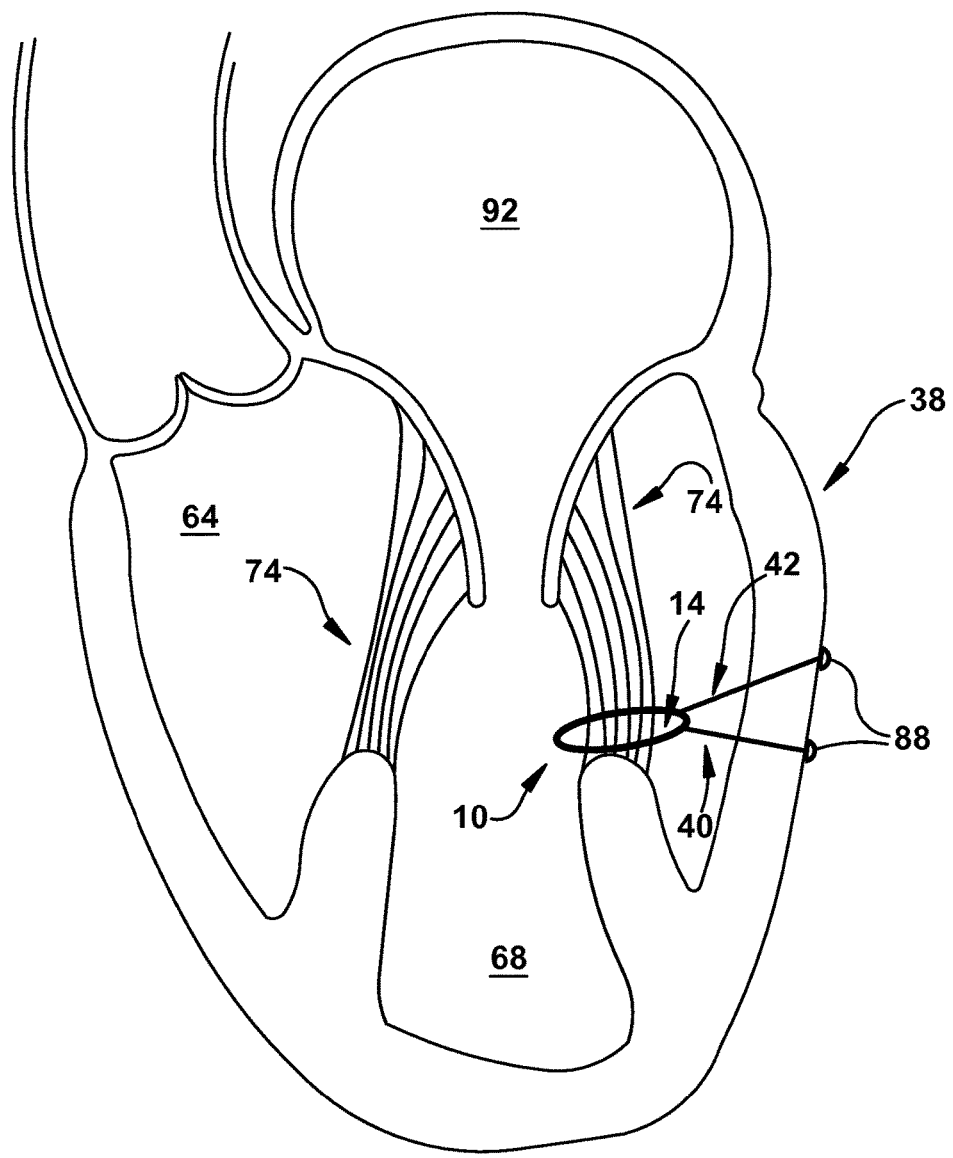
FIG. 14 is a schematic side view of an alternative configuration of the device of FIGS. 1A-1B.

In FIG. 14, another alternative configuration of the device 10 is shown, with a single central chordae support portion 14 being anchored directly to the left ventricle posterior-lateral wall by the first and second anchoring catheters 40 and 42, with no other tensioning structures being provided within the left ventricle 68.

Figure 15A:
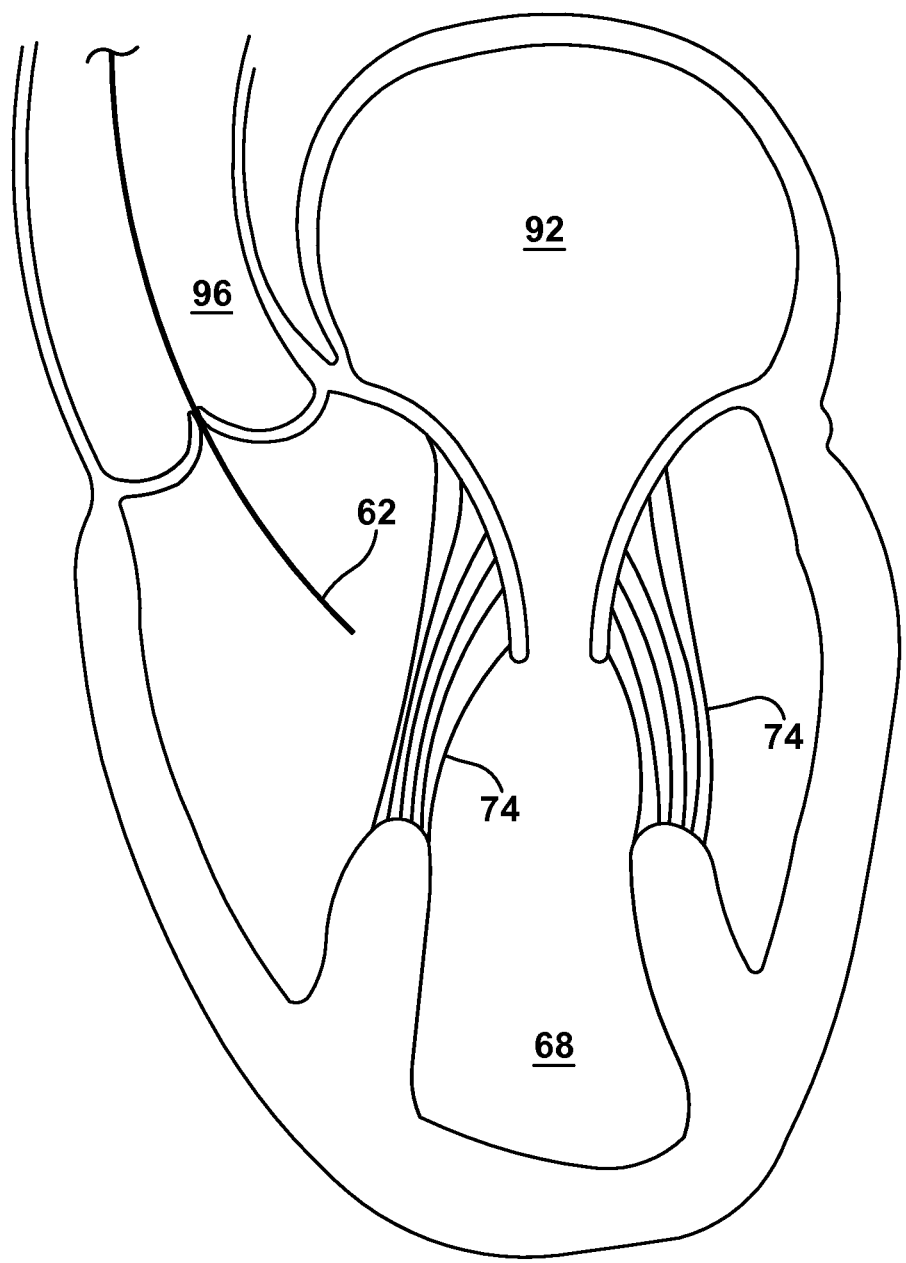
FIGS. 15A-15E schematically depict a sequence of operation of the device of FIGS. 1A-1B.
Figure 15B:
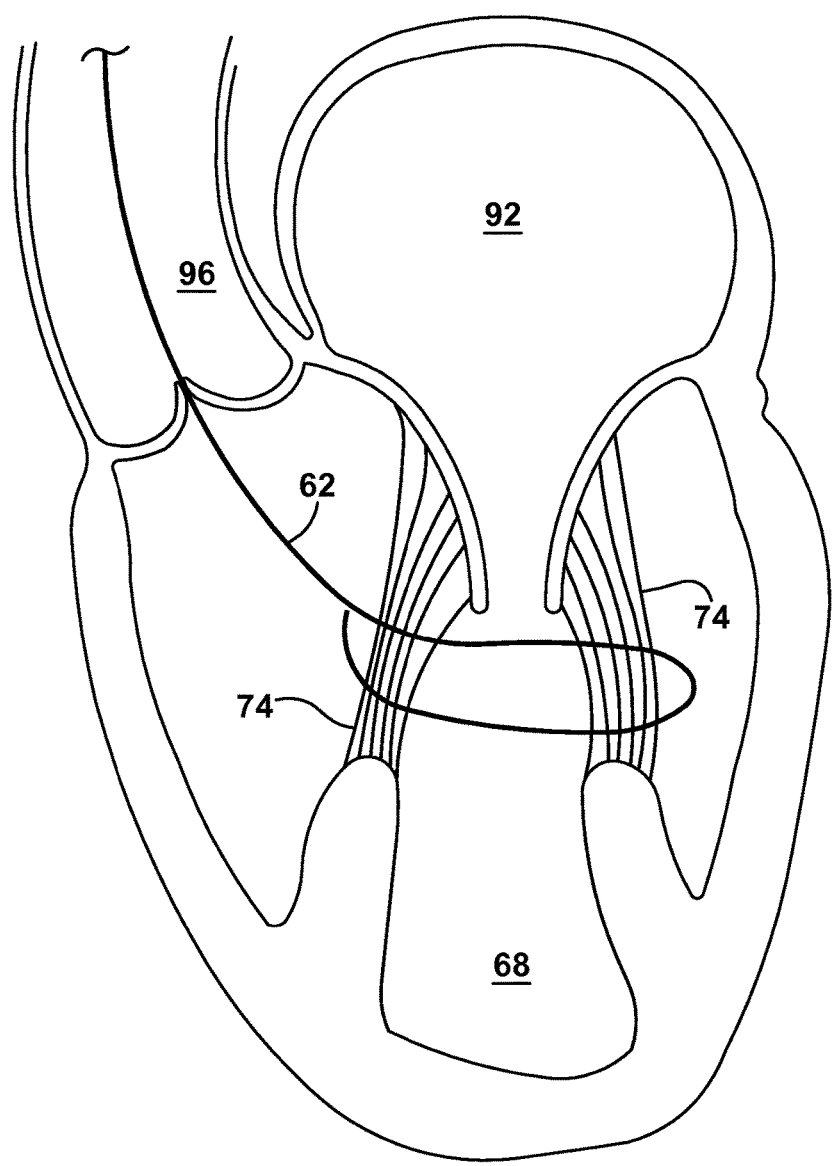
Figure 15C:
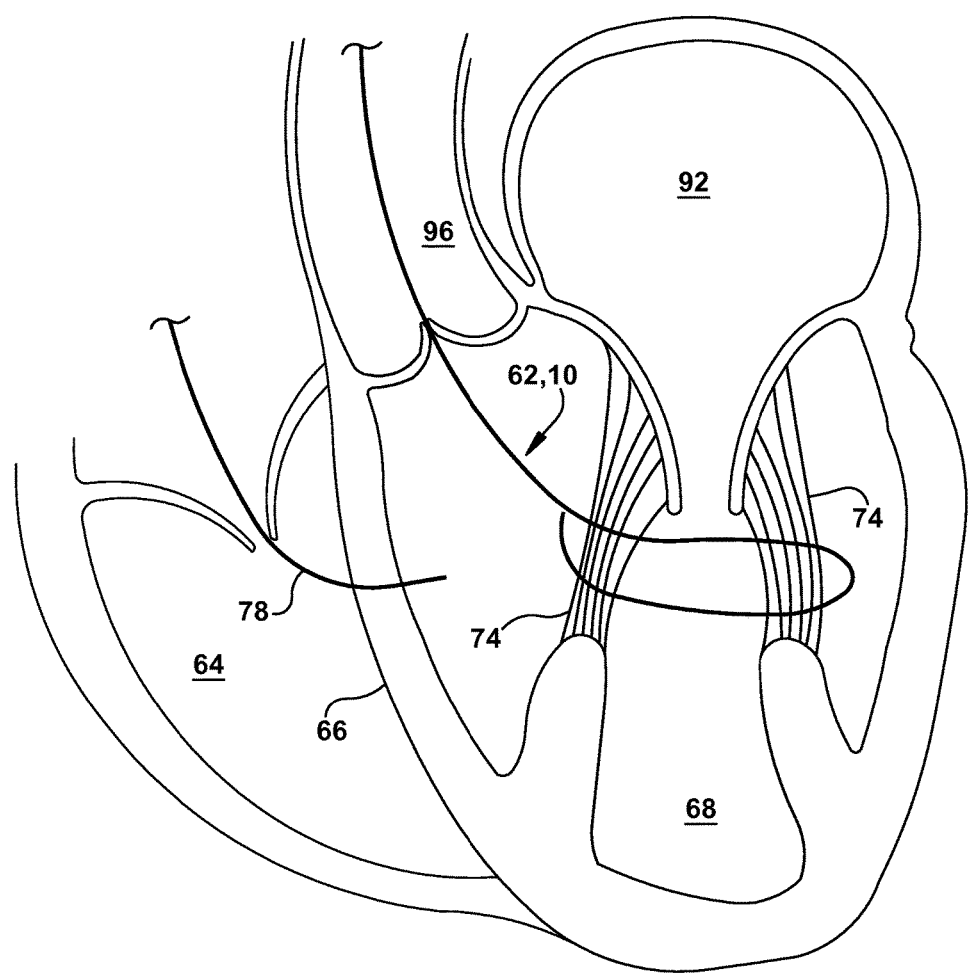

The sequence of FIGS. 15A-15E schematically depicts placement of any configuration of the device 10 via a trans interventricular septal approach which is otherwise similar to the sequence depicted in FIGS. 6-8. In FIG. 15A, a first guidewire 62 is passed through the aorta 96 and into the left ventricle 68. In FIG. 15B, a loop is made around the chordae tendineae 74 with the guidewire 62. FIG. 15C depicts a second guidewire 78 approaching the interventricular septum 66 from the right ventricle 64—the first guidewire 62 could still be maintained in the loop, and/or at least a portion of the device 10 may have already been passed over the first guidewire 62 to achieve the looped structure shown in FIG. 15C.

Figure 15D:
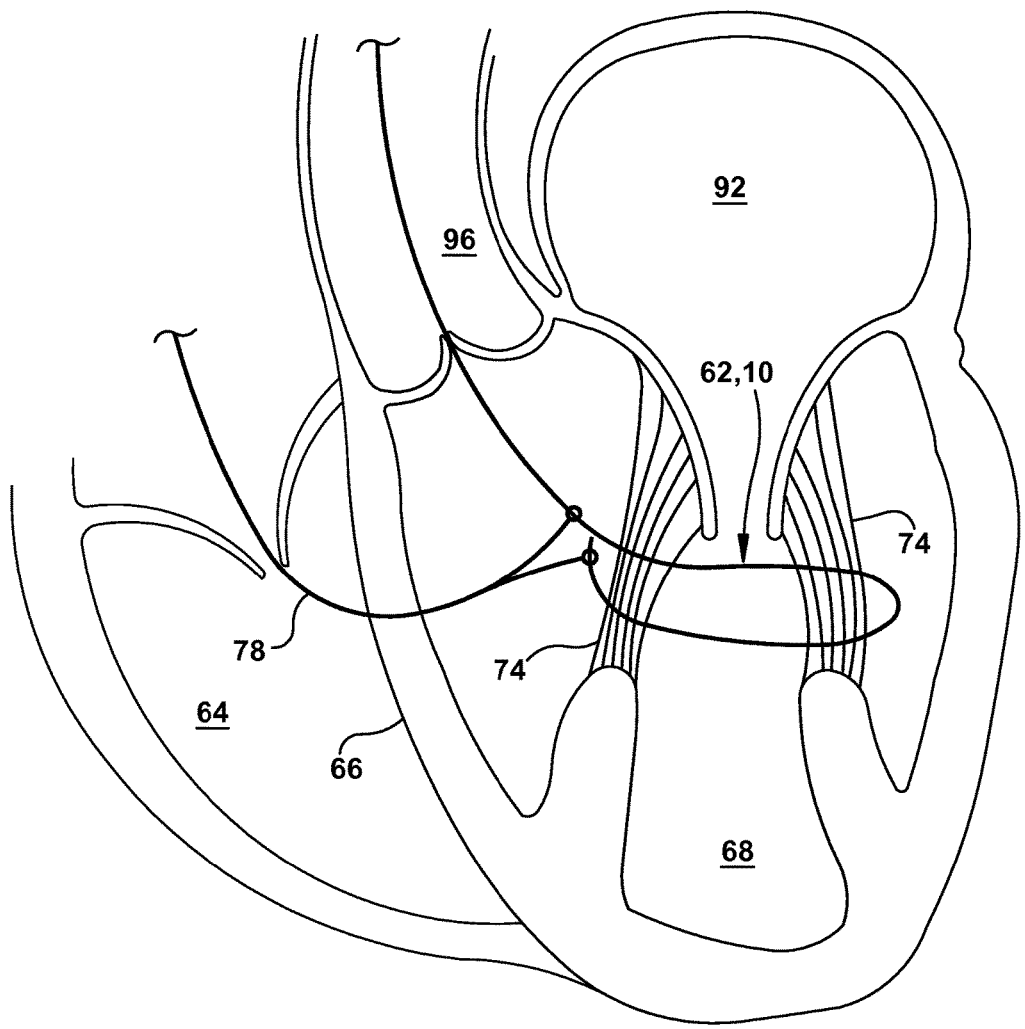
Figure 15E:
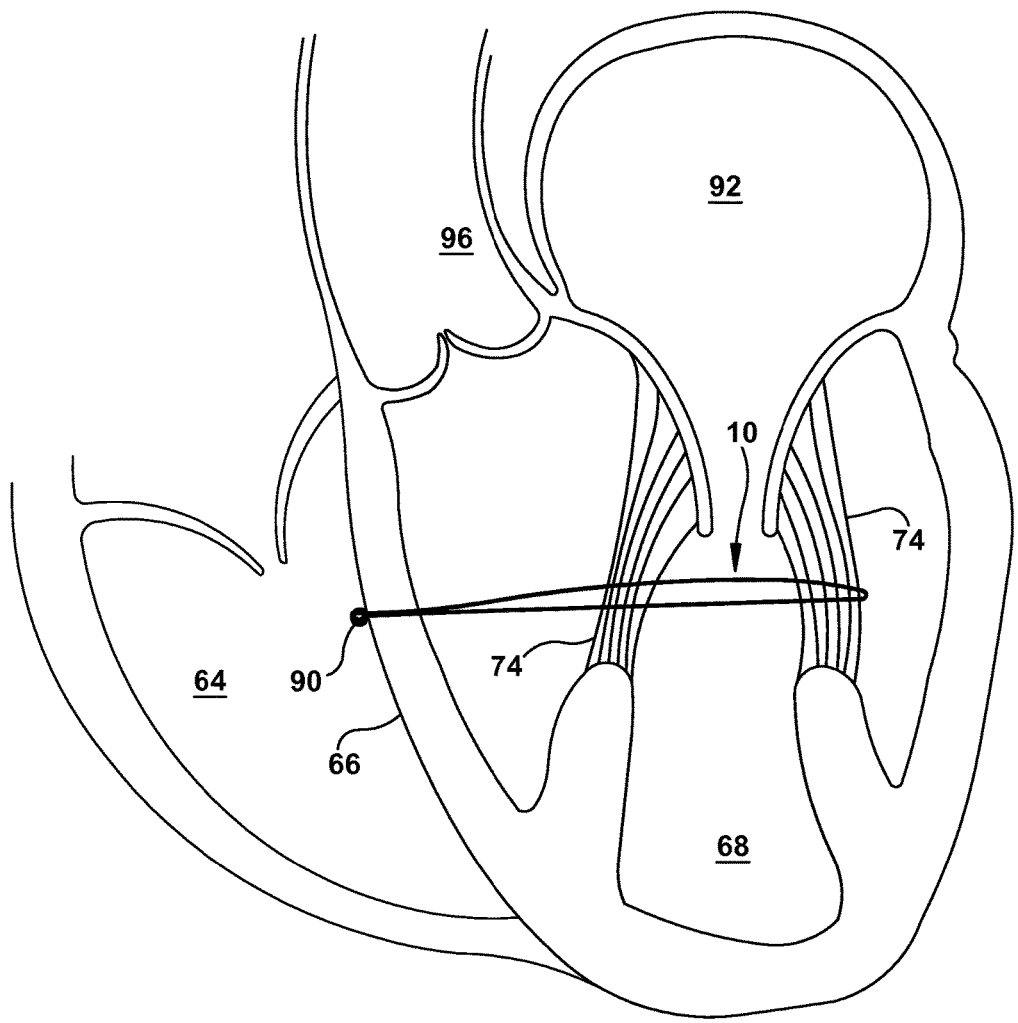

Turning to FIG. 15D, the second guidewire 78 (optionally with the assistance of another guidewire, not shown) "catches" two portions of the loop formed by the first guidewire 62 and/or the device 10 in any suitable manner, consecutively or concurrently. FIG. 15E, then, shows the device 10 as installed with one or more internal right ventricle anchors 90, similar to the arrangement shown in FIG. 9, with or without the addition of the external left ventricle anchors.

Figure 16:
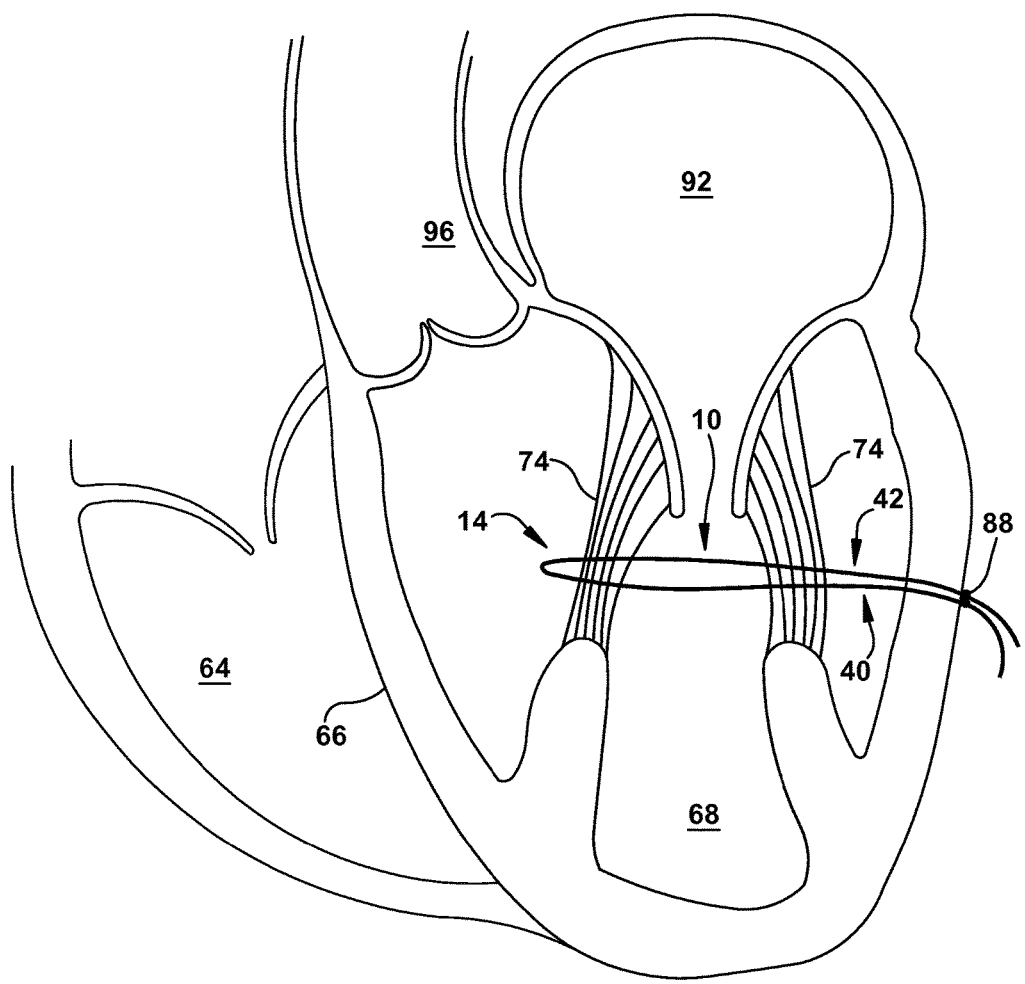
FIG. 16 schematically depicts the device in FIGS. 1A-1B in an alternative configuration.

In FIG. 16, another alternative configuration of the device 10 is shown, with a single central chordae support portion 14 being anchored directly to the left ventricle posterior-lateral wall by the first and second anchoring catheters 40 and 42, after the heart has been accessed pericardially.

In summary, the device 10, system 38, and/or method 44 described and depicted herein can help normalize and remodel the leaflet shape and function, correct the leaflet mobility, coapt by improving the leaflet closure movement during systole, and/or corrects the unbalance angle of leaflet coaptation and sub-valvular apparatus position for valve regurgitation, without removing leaflet tissue, chordal shortening, transposing or replacement, placating and deforming the valve annulus, or using other surgical techniques or sophisticated procedures for making the valve competent. The device 100 can be adjustable depending on the anatomic leaflet and sub-valvular apparatus configuration, and the free-edge leaflet coaptation angle, to obtain normal correction by mechanical or electromagnetic adjustment through a flexible catheter by echo guidance, or by transcatheter or percutaneous approach with a flexible electromagnetic or mechanical adjustment catheter by transeptal, trans atrial, trans apical, and/or trans ventricular approach under echocardiographic guidance.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials, such as, but not limited to, metal, plastic, Elgiloy, Nitinol, stainless steel, titanium, pyrrolitic carbon, and the like, or any combination thereof; however, the chosen material(s) should be biocompatible (and/or covered/coated with synthetic or natural biological and biocompatible materials) for many applications. Any structure described herein could be at least partially coated, impregnated with, or otherwise provided with pharmacologic and/or biologic agents, which may be permitted or designed to leach or otherwise disperse into surrounding patient tissue structures. Any of the described structures and components could be disposable or reusable as desired for a particular use environment. Any component could be provided with a user-perceptible marking to indicate a material, configuration, at least one dimension, or the like pertaining to that component, the user-perceptible marking aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

The following is claimed:

1. A system for treating a regurgitant heart valve in a subject, the system comprising:
    a flexible, elongated body having a central chordae support portion and first and second arms, the central chordae support portion being disposed between, and connected directly to, the first and second arms, the first and second arms including first and second lumens, respectively, extending longitudinally therethrough;
    a first anchoring catheter disposed in, and extending through, the first lumen, the first anchoring catheter including proximal and distal ends; and
    a second anchoring catheter disposed in, and extending through, the second lumen, the second anchoring catheter including proximal and distal ends;
    wherein the distal ends of the first and second anchoring catheters are located distally from the first and second lumens, respectively, and the proximal ends of the first and second anchoring catheters are located proximally to the first and second lumens, respectively, such that the first and second lumens are longitudinally interposed between the proximal and distal ends of the first and second anchoring catheters.

2. The system of claim 1, wherein first and second ends of each of the first and second anchoring catheters are configured for attachment to the interventricular septum and the postero-lateral left ventricular wall, respectively.

3. The system of claim 1, wherein the body is shaped and dimensioned like a chin strap, with the central chordae support portion having a maximum height at approximately a midsection of a length of the central chordae support portion, a height of the central chordae support portion tapering from the maximum height toward sides of the central chordae support portion adjacent the first and second arms.

4. The system of claim 1, wherein the body is sling-shaped, with the central chordae support portion being shorter than each of the first and second arms.

5. The system of claim 1, wherein the central chordae support portion includes at least one contact surface configured to directly contact one or more chordae tendineae, the at least one contact surface having an area that is greater than a footprint of the first and/or second arms.

6. The system of claim 1, wherein the central chordae support portion includes oppositely disposed top and bottom surfaces, with one or more apertures extending through the central chordae support portion, between the top and bottom surfaces.

7. The system of claim 1, wherein the central chordae support portion includes at least one contact surface configured to directly contact one or more chordae tendineae, the at least one contact surface having an area that is less than a footprint of the first and/or second arms.

8. The system of claim 1, wherein the first and second anchoring catheters remain indwelling within a heart of the subject for as long as the central chordae support portion is extant therein.

9. The system of claim 1, wherein the elongated body is a single, unitary structure comprising the first and second arms integrally formed with, and from the same material as, the central chordae support portion.

* * * * *